United States Patent [19]

Barth

[11] Patent Number: 4,502,990

[45] Date of Patent: Mar. 5, 1985

[54] PROCESS FOR 6-(AMINOMETHYL)PENICILLANIC ACID 1,1-DIOXIDE AND DERIVATIVES THEREOF

[75] Inventor: Wayne E. Barth, East Lyme, Conn.

[73] Assignee: Pfizer Inc., New York, N.Y.

[21] Appl. No.: 501,476

[22] Filed: Jun. 6, 1983

[51] Int. Cl.$^3$ .................. C07D 499/00; A61K 31/425
[52] U.S. Cl. ...................... 260/245.2 R; 260/245.2 T; 260/239.1
[58] Field of Search ...................... 260/239.1, 245.2 T, 260/245.2 R; 424/270, 271

[56] References Cited

U.S. PATENT DOCUMENTS

| 4,207,323 | 6/1980 | Beattie et al. | 424/270 |
| 4,234,579 | 11/1980 | Barth | 424/246 |
| 4,237,051 | 12/1980 | McCombie | 260/245.2 |
| 4,287,181 | 9/1981 | Kellogg | 424/114 |
| 4,309,347 | 1/1982 | Bigham | 260/245.2 |

FOREIGN PATENT DOCUMENTS 2053220 2/1981 United Kingdom .

OTHER PUBLICATIONS

DiNinno et al., J. Org. Chem., 42, pp. 2960–2965, (1977).

Primary Examiner—Nicholas S. Rizzo
Attorney, Agent, or Firm—Charles J. Knuth; Albert E. Frost; Robert K. Blackwood

[57] ABSTRACT

A process for the preparation of beta-lactamase inhibiting 6-alpha-(aminomethyl)penicillanic acid 1,1-dioxide and derivatives. R- and S-1-(ethoxycarbonyloxy)ethyl 6-alpha-(aminomethyl)penicillanate 1,1-dioxide are specifically described.

20 Claims, No Drawings

PROCESS FOR 6-(AMINOMETHYL)PENICILLANIC ACID 1,1-DIOXIDE AND DERIVATIVES THEREOF

BACKGROUND OF THE INVENTION

An alternative process for the synthesis of 6-alpha-(aminomethyl)penicillanic acid and its derivatives is described. This process proceeds stereospecifically from 6-alpha-bromopenicillanate 1,1-dioxide esters, via the corresponding 6-alpha-bromomagnesium Grignard reagent and the 6-alpha(benzyloxycarbonylaminomethyl) derivative. This synthesis is of particular value in the preparation of diastereomeric R- and S-1-(ethoxycarbonyloxy)ethyl 6-alpha-(aminomethyl)-penicillanate 1,1-dioxide.

My co-pending U.S. patent application Ser. No. 434,371, filed Oct. 21, 1982 now U.S. Pat. No. 4,452,796 describes alternative processes for 6-alpha-(aminomethyl)penicillanic acid 1,1-dioxide, salts thereof, and certain esters thereof which are hydrolyzable under physiological conditions; and further describes the antibacterial utility of these compounds, principally as beta-lactamase inhibitors useful in combination with conventional beta-lactam antibiotics.

The present process is particularly advantageous in the synthesis of R- and S-1-(ethoxycarbonyloxy)ethyl 6-alpha-(aminomethyl)penicillanate 1,1-dioxide. Although in my above cited earlier application, I have generally described 1-(ethoxycarbonyloxy)ethyl esters, I did not describe the present, highly valuable R- and S-diastereoisomers, which are now efficiently available by the present novel process.

Other compounds previously reported as beta-lactamase inhibitors useful in combination with beta-lactam antibiotics for the treatment of bacterial infections include penicillanic acid 1,1-dioxide and esters thereof readily hydrolyzable in vivo (Barth, U.S. Pat. No. 4,234,579); the bis-methanediol ester of sulbactam (Bigham, U.S. Pat. No. 4,309,347); various 6-beta-(hydroxymethyl)penicillanic acid 1,1-dioxides and esters thereof (Kellogg, U.S. Pat. No. 4,287,181); and 6-beta-(aminomethyl)penicillanic acid (McCombie, U.S. Pat. No. 4,237,051).

U.K. Patent Application No. 2,053,220, published Feb. 4, 1981, broadly discloses beta-lactamase inhibiting compounds of the formula

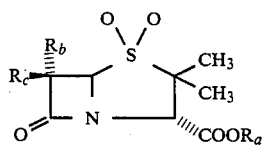

The definitions of $R_a$, $R_b$ and $R_c$ define literally an infinite number of compounds. These definitions, by appropriate selection of $R_a$, $R_b$ and $R_c$, may possibly define the 6-alpha-(aminomethyl)penicillanic acid 1,1-dioxides of present interest. No specific method for preparation of these compounds is present in the disclosure of this U.K. application, and there is no hint or suggestion that from among the infinity of compounds proposed, the present aminomethyl compounds are preferred compounds, possessing the particularly highly potent beta-lactamase inhibitory activity which we have determined for them.

DiNinno et al., J. Org. Chem. 42, pages 2960–2965 (1977) [see also Beattie et al., U.S. Pat. No. 4,207,323 (1980)] have previously described structurally related Grignard reagents derived from 6-alpha-bromopenicillanates (reacted with acetaldehyde), likewise formed at low temperatures. The present Grignard reagents derived from 6-alpha-bromopenicillanate 1,1-dioxides are distinguished thereover by the surprising fact that it has been found possible to retain 6-alpha-stereochemistry in the derived Grignard reagent.

Concurrently filed U.S. patent application Ser. No. 501,475 for "beta-Lactamase Inhibiting 6-(Alkoxyaminomethyl)penicillanic Acid 1,1-Dioxide and Derivatives" by D. K. Pirie et al. discloses a further useful process for 6-alpha-(aminomethyl)penicillanic acid 1,1-dioxide and derivatives, which proceeds via the present, sterically stable Grignard reagents derived from 6-alpha-bromopenicillanate ester 1,1-dioxides.

SUMMARY OF THE INVENTION

The present invention relates to a process for the preparation of a compound of the formula

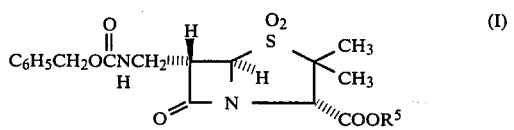

wherein $R^5$ is a conventional carboxy protecting group removable by hydrogenolysis, or a conventional ester forming radical which is hydrolyzable under physiological conditions, which comprises reacting a compound of the formula

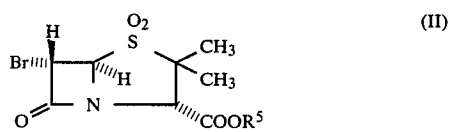

with substantially 2 molar equivalents of methylmagnesium bromide and then 1 molar equivalent of benzyl N-(acetoxymethyl)carbamate at $-50°$ to $-100°$ C. in an ethereal solvent.

As detailed below, the compounds of the formula (I) are useful as intermediates in the synthesis of beta-lactamase inhibiting 6-alpha-(aminomethyl)penicillanic acid 1,1-dioxide and esters hydrolyzable under physiological conditions.

The reference to esters which are hydrolyzable under physiological conditions refers to those esters frequently referred to as "pro-drugs". Such esters are now as well-known and common in the penicillin art as pharmaceutically-acceptable salts. Such esters are generally used to enhance oral absorption, but in any event are readily hydrolyzed in vivo to the parent acid, having beta-lactamase inhibitory activity. Preferred esters show no tendency to hydrogenolyze under the conditions presently employed for their preparation (see below). The more preferred ester forming radicals are:
gamma-butyrolacton-4-yl,
—CHR²OCOR³, and
—CHR²OCOOR³,
wherein $R^2$ is hydrogen or methyl and $R^3$ is $(C_1-C_6)$alkyl. The presently most preferred radicals are 1-R- and 1-S-ethoxycarbonyloxyethyl.

Conventional carboxyl protecting groups removable by hydrogenolysis include, but are not limited to such groups as benzyl, benzhydryl and 2-naphthylmethyl. These groups are readily introduced and removed by catalytic hydrogenolysis, using conventional methods well known in the art.

The above-mentioned ethereal solvent refers to such well known solvents as diethyl ether, diisopropyl ether, dioxane and tetrahydrofuran; or mixtures thereof. A solvent comprised principally of tetrahydrofuran is preferred since it is liquid over the entire preferred temperature range, and sufficiently non-volatile to be handled with relative safety, yet sufficiently volatile to be readily removed and recovered.

The present invention also encompasses a Grignard reagent of the formula

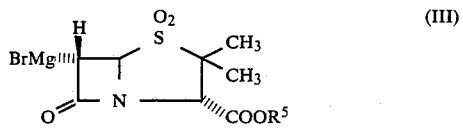

wherein
$R^5$ is as defined above;
1-R- or 1-S-(ethoxycarbonyloxy)ethyl 6-alpha-(benzyloxycarbonylaminomethyl)penicillanate 1,1-dioxide; and
1-R- or 1-S-(Ethoxycarbonyloxy)ethyl 6-alpha-(aminomethyl)penicillanate 1,1-dioxide, and the pharmaceutically acceptable acid addition salts thereof.

When dosed orally in rats, the latter aminomethyl compounds show exceptionally high blood levels of alpha-(aminomethyl)penicillanic acid 1,1-dioxide, demonstrating unusually high oral absorption and in vivo hydrolysis of the ester group.

The above-mentioned pharmaceutically-acceptable acid addition salts include, but are not limited to, those with hydrochloric acid, sulfuric acid, nitric acid, phosphoric acid, citric acid, maleic acid, succinic acid, benzenesulfonic acid, p-toluene sulfonic acid, 2-naphthalenesulfonic acid and methanesulfonic acid. Pharmaceutically-acceptable cationic salts include, but are not limited to, those of sodium, potassium, calcium, N,N'-dibenzylethylenediamine, N-methylglucamine (meglumine) and diethanolamine.

As employed herein, the expression "reaction-inert solvent" refers to a solvent which does not interact with reactants or products in a manner which adversely affects the yield of the desired product.

DETAILED DESCRIPTION OF THE INVENTION

The present process for conversion of compounds of the above formula (II) to (I) is readily carried out with retention of 6-alpha stereochemistry as noted above. The process is generally carried out in two stages, both at $-50°$ to $-100°$ C. in an ethereal solvent.

In the first stage, the alpha-bromoester (II), dissolved in an ethereal solvent, is treated with an ethereal solution of at least one equivalent of a Grignard reagent such as methylmagnesium bromide (formed by standard methods in the laboratory, or purchased commercially), generally added portionwise over a few minutes while maintaining the low temperature of the reaction. In this manner Grignard reagent of the formula (III) above is formed in situ. Since the second stage process requires the presence of a second equivalent of methylmagnesium bromide, it is most convenient to simply use substantially two equivalents of methylmagnesium bromide in the first stage of the process.

The above first stage of the process occurs rapidly at the specified temperature. In order to minimize any undesirable side reactions, it is preferred to proceed immediately, or within a few minutes, to the second stage of the process which, with the second equivalent of methylmagnesium bromide already present, simply involves addition of substantially one equivalent of benzyl N-(acetoxymethyl)carbamate, having the formula

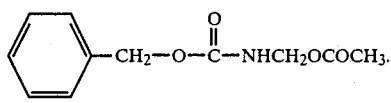

The second stage of the process also occurs rapidly at the specified temperature, and within a few minutes the reaction can be quenched, e.g., by the addition of excess glacial acetic acid, and the product isolated by standard methods such as evaporation, extraction and chromatography.

As noted above, the resulting compounds of the formula (I) are useful as intermediates for the preparation of 6-alpha-(aminomethyl)penicillanic acid 1,1-dioxide of the formula

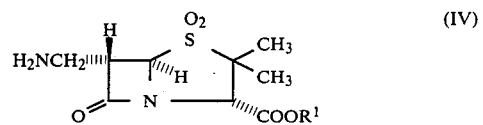

wherein $R^1$ is hydrogen or a conventional ester forming radical which is hydrolyzable under physiological conditions; a pharmaceutically acceptable acid addition salt thereof; or a pharmaceutically acceptable cationic salt thereof when $R^1$ is hydrogen.

Thus esters of the formula (I) wherein $R^5$ is a conventional carboxy protecting group removable by hydrogenolysis are converted by hydrogenolysis to the compounds (IV) wherein $R^5$ is hydrogen while those esters of the formula (I) wherein $R^5$ is an in vivo hydrolyzable ester forming radical are converted by hydrogenolysis to compounds of the formula (IV) wherein $R^1$ is retained in the form of that ester function.

The above hydrogenolysis is carried out by methods well-known in the penicillin art. The substrate, in a reaction-inert solvent, is contacted with hydrogen in the presence of a noble metal catalyst, such as palladium, platinum or rhodium, optionally in the form of its oxide or a salt, or on a carrier such as carbon, an alkaline earth carbonate or alumina. Temperature is not critical (e.g. $0°-50°$ C.) but is preferably $25°$ C. or lower in order to minimize thermal degradation. Pressure can be varied over a wide range (subatmospheric to 100 atmospheres), but as a matter of convenience will generally be in the range of 1 to 7 atmospheres. The reaction inert solvent is preferably relatively low boiling so as to be readily removed by concentration in vacuo. Aqueous tetrahydrofuran is a solvent particularly well-suited for the present purpose. The preferred catalyst is palladium supported on carbon.

When $R^5$ is an in vivo hydrolyzable ester, it is preferable that the hydrogenolysis is carried at a pH below 6 in order to avoid possible hydrolysis of the sensitive ester group. If desired, the hydrogenation is carried out in the presence of up to about one equivalent of an acid (e.g., HCl, p-toluenesulfonic acid), or in the presence of a weakly acidic buffer comprising equimolar quantities of a weakly basic amine, such as pyridine, and a strong acid such as a mineral acid (e.g., HCl, $HNO_3$, $H_2SO_4$) or preferably a sulfonic acid (such as methanesulfonic acid, benzenesulfonic acid or p-toluenesulfonic acid), otherwise according to methods described above.

The above-defined pharmaceutically-acceptable acid addition salts of the present invention are readily prepared by standard methods. For example, an equivalent of the acid is combined with the free amine form of the compound in an organic or aqueous organic solvent. The salt is isolated by concentration and/or the addition of a non-solvent. As noted above, the salt is alternatively isolated directly from a reaction mixture, i.e., without isolation of the free amine, otherwise using similar techniques of concentration and/or addition of a nonsolvent.

The above-defined pharmaceutically-acceptable cationic salts of those compounds of the present invention having a free carboxylic acid group are also readily prepared by standard methods. For example, an equivalent of the corresponding cationic hydroxide, carbonate or bicarbonate, or an amine is combined with the carboxylic acid in an organic or aqueous solvent, preferably at reduced temperature (e.g. 0°-5° C.), with vigorous agitation and slow addition of the base. The salt is isolated by concentration and/or the addition of a non-solvent. In some cases, the salt is isolated directly from a reaction mixture, without isolation of the free acid form.

The starting materials of the formula (II) required for the above process are generally derived ultimately from 6,6-dibromopenicillanic acid, applying the unit process steps of:

(1) 6-beta-debromination to form the alpha-6-bromo compound;
(2) esterification to form the hydrogenolyzable or in vivo hydrolyzable ester; and
(3) oxidation to form the 1,1-dioxide.

Generally, any sequence of these steps may be used, although when $R^5$ is a hydrolyzable ester, it is preferred to carry out the steps in the indicated sequence.

The above debromination step is preferably carried out by the action of sodium bisulfite, as exemplified below and as disclosed in currently filed U.S. application, Ser. No. 501,731 filed June 6, 1983 for "Process for Debromination of Dibromopenicillanic Acid and Derivatives" by Pirie et al. The 1,1-dioxidation is conveniently carried out using at least two equivalents of a peracid (conveniently m-chloroperbenzoic acid) in a reaction inert solvent such as ethyl acetate at 0°-50° C. The ester group is readily introduced by methods well known to those skilled in the penicillin art (see for example, U.S. Pat. Nos. 4,234,579; 4,287,181; and 4,348,264).

Some of the compounds of the formulae (IV), generally those wherein $R^1$ is hydrogen, have in vitro antibacterial activity. Such activity is demonstrated by measuring the minimum inhibitory concentrations (MIC's) in mcg/ml against a variety of microorganisms. The procedure which is followed is the one recommended by the International Collaborative Study on Antibiotic Sensitivity Testing (Ericcson and Sherris, *Acta. Pathologica et Microbiologia Scandinav*, Supp. 217, Section B: 64-68 [1971]), and employs brain heart infusion (BHI) agar and the inocula replicating device. Overnight growth tubes are diluted 100 fold for use as the standard inoculum (20,000–10,000 cells in approximately 0.002 ml are placed on the agar surface; 20 ml of BHI agar/dish). Twelve 2 fold dilutions of the test compound are employed, with initial concentration of the test drug being 200 mcg/ml. Single colonies are disregarded when reading plates after 18 hours at 37° C. The susceptibility (MIC) of the test organism is accepted as the lowest concentration of compound capable of producing complete inhibition of growth as judged by the naked eye.

Those compounds of the formulae (IV) having said in vitro antibacterial activity are thus useful as industrial antimicrobials, for example in water treatment, slime control, paint preservation and wood preservation, as well as for topical application as a disinfectant. In the case of use of these compounds for topical application, it is often convenient to admix the active ingredient with a non-toxic carrier, such as vegetable or mineral oil or an emollient cream. Similarly, it can be dissolved or dispersed in liquid diluents or solvents such as water, alkanols, glycols or mixtures thereof. In most instances it is appropriate to employ concentrations of the active ingredient of from about 0.1 percent to about 10 percent by weight, based on total composition.

The compounds of the formulae (IV) are of more particular value as potent inhibitors of microbial beta-lactamases. By this mechanism they increase the antibacterial effectiveness of beta-lactam antibiotic (penicillins and cephalosporins) against many microorganisms, particularly those which produce a beta-lactamase. The ability of these compounds to increase the effectiveness of a beta-lactam antibiotic can be appreciated by reference to experiments in which the MIC values of the antibiotic alone, and a compound of the formula (IV) (having $R^1$ as hydrogen) alone, are determined. These MIC's are then compared with the MIC values obtained with a combination of the given antibiotic and the compound of the formula (IV), wherein $R^1$ is hydrogen. When the antibacterial potency of the combination is significantly greater than would have been predicted from the potencies of the individual compounds, this is considered to constitute enhancement of activity. The MIC values of combinations are measured using the method described by Barry and Sabath in "Manual of Clinical Microbiology", edited by Lenette, Spaulding and Truant, 2nd Edition, 1974, American Society for Microbiology.

The compounds of the formulae (IV) enhance the antibacterial effectiveness of beta-lactam antibiotics in vivo. That is, they lower the amount of the antibiotic which is needed to protect mice against an otherwise lethal inoculum of certain beta-lactamase producing bacteria. In determining such activity, acute experimental infections are produced in mice by the intraperitoneal inoculation of the mice with a standardized culture of the test organism suspended in 5 percent hog gastric mucin. Infection severity is standardized so that the mice receive a lethal dose of the organism (the lethal dose is the minimum inoculum of organism required to consistently kill mice. A mixture of compound of the formula (IV) and beta-lactam 100 percent of the infected, non-treated control antibiotic is administered at various dosage levels, p.o. or i.p., to groups of infected mice. At the end of the test, the activity of the mixture is assessed by counting the number of survivors among treated animals at a given dose. Activity is expressed as the percentage of animals which survive at a given dose, or calculated as a $PD_{50}$ (dose which protects 50% of the animals from infection).

The utility of compounds of the formula (IV) is alternatively assessed by a determination of blood levels following oral or parenteral dosage. Rats represent a convenient animal model for this purpose. When dosed as an in vivo hydrolyzable ester, the blood level is determined as the parent compound wherein $R^1$ is hydrogen. The blood level is determined by serial dilution bioassay technique using a microorganism such as *Pasturella multocida* which shows particular sensitivity to the parent compound.

The ability of the compounds of formulae (IV) to enhance the effectiveness of a beta-lactam antibiotic against beta-lactamase producing bacteria makes them valuable for co-administration with beta-lactam antibiotics in the treatment of bacterial infections in mammals, particularly man. In the treatment of a bacterial infection, the compound of the formula (IV) can be co-mingled with the beta-lactam antibiotic, and the two agents thereby administered simultaneously. Alternatively, the compound of the formula (IV) can be administered as a separate agent during a course of treatment with a beta-lactam antibiotic. In some instances it will be advantageous to pre-dose the subject with the compound of the formula (IV) before initiating treatment with a beta-lactam antibiotic.

When using a compound of formula (IV) to enhance the effectiveness of beta-lactam antibiotic, a mixture of (IV) with the beta-lactam antibiotic is administered preferably in formulation with standard pharmaceutical carriers or diluents. A pharmaceutical composition comprising a pharmaceutically acceptable carrier, a beta-lactam antibiotic and a compound of formula (IV) will normally contain from about 5 to about 80 percent of the pharmaceutically acceptable carrier by weight.

When using the compounds of formula (IV) in combination with another beta-lactam antibiotic, said compounds can be administered orally or parenterally, i.e., intramuscularly, subcutaneously or intraperitoneally. Although the prescribing physician will ultimately decide the dosage to be used in a human subject, the ratio of the daily dosages of the compounds of formula (IV) and the beta-lactam antibiotic will normally be in the range from about 1:3 to 3:1 by weight. Additionally, when using the compounds of formula (IV) in combination with another beta-lactam antibiotic, the daily oral dosage of each component will normally be in the range from about 10 to about 200 mg per kilogram of body weight and the daily parenteral dosage of each component will normally be about 10 to about 40 mg per kilogram of body weight. These daily doses will usually be divided. In some instances, the prescribing physician will determine that dosages outside these limits are necessary.

As will be appreciated by one skilled in the art, some beta-lactam compounds are effective when administered orally or parenterally, while others are effective only when administered by the parenteral route. When a compound of formula (IV) is to be used simultaneoulsy (i.e., co-mingled) with a beta-lactam antibiotic which is effective only on parenteral administration, a combination formulation suitable for parenteral use will be required. When a compound of formula (IV) is to be used simultaneously (co-mingled) with a beta-lactam antibiotic which is effective orally or parenterally, combinations suitable for either oral or parenteral administration can be prepared. Additionally, it is possible to administer preparations of the compounds of formula (IV) orally, while at the same time administering a further beta-lactam antibiotic parenterally; and it is also possible to administer preparations of the compounds of formula (IV) parenterally, while at the same time administering the further beta-lactam antibiotic orally.

The present invention is illustrated by the following examples. However, it should be understood that the invention is not limited to the specific details of these examples. Unless otherwise specified, all operations were carried out at ambient temperatures; all temperatures are in °C., all drying of solutions was over anhydrous $Na_2SO_4$; all solvent evaporations were carried out in vacuo; all pnmr (proton nuclear magnetic resonance) spectra were at 60 MHz unless otherwise specified. The abbreviations DMF, TEA, THF and DMSO are used, respectively, for N,N-dimethylformamide, triethylamine, tetrahydrofuran and dimethylsulfoxide.

EXAMPLE 1

Benzyl 6-alpha-(Benzyloxycarbonylaminomethyl)penicillanate 1,1-Dioxide

Benzyl 6-alpha-bromopenicillanate 1,1-dioxide (0.804 g., 2.0 mmoles) in 30 ml. dry THF was cooled to $-78°$. Ethereal $CH_3MgBr$ (2.8M, 1.43 ml., 4.0 mmoles) was added over 3 minutes and stirring continued for 7 minutes at $-78°$, forming the corresponding 6-alpha-bromomagnesium Grignard reagent. A solution of benzyl N-(acetoxymethyl)carbamate (0.57 g., 2.0 mmole) in 5 ml. dry THF was then added. After stirring 5 minutes at $-78°$, the reaction mixture was quenched by the addition of 0.5 ml. $CH_3CO_2H$, the solvent evaporated and the residue taken up in $CHCl_3$, washed with $H_2O$, saturated $NaHCO_3$ and brine, dried and evaporated to a viscous oil (1.1 g.). The oil was chromatographed on 40 g. silica gel eluting with 1:19 ethyl acetate:chloroform in 20 ml. fractions. Fractions 5-8 were combined, evaporated to an oil (0.55 g.) which was crystallized by scratching in 10 ml. ether; 0.32 g.; pnmr/$CDCl_3$/delta/TMS 1.20 (3H, s), 1.49 (3H, s), 3.65 (3H, m), 4.32 (1H, s), 4.59 (1H, m), 5.07 (2H, s), 5.14 (2H, q), 5.30 (1H, br), 7.32 (10H, s).

By the same procedure, benzhydryl 6-alpha-bromopenicillanic acid 1,1-dioxide is converted to benzhydryl 6-alpha-benzyloxycarbonylaminomethyl)-penicillanate 1,1-dioxide.

EXAMPLE 2

6-alpha-(Aminomethyl)penicillanic Acid 1,1-Dioxide

Title product of preceding Example (1.7 g.), THF (35 ml.), $H_2O$ (35 ml.) and 10% Pd/C (1.7 g.) were combined and hydrogenated at 50 psig for 1 hour. Catalyst was recovered by filtration and THF removed from the filtrate in vacuo. The aqueous layer was washed with 30 ml. ethyl acetate, and the aqueous layer concentrated to yield crystalline title product; 0.7 g.; pnmr/250 MHz/$D_2O$/DSS 1.44 (3H, s), 1.59 (3H, s), 3.63 (2H, d, J=5.5 Hz), 4.07 (1H, td, J=2, 5.5 Hz), 4.31 (1H, s), 5.06 (1H, d, J=2).

The same product is obtained by hydrogenolysis of the benzydryl ester of the preceding Example.

EXAMPLE 3

S-1-(Ethoxycarbonyloxy)ethyl 6-alpha-(Benzyloxycarbonylaminomethyl)penicillanate 1,1-Dioxide S-1-(Ethoxycarbonyloxy)ethyl 6-alpha-bromopenicillanate 1,1-dioxide (16.8 g., 0.0392 mole) was dissolved in 150 ml. dry THF and cooled to −78° C. Ethereal $CH_3MgBr$ (2.9M, 24.3 ml., 0.0706 mole) was added over 5 minutes (to form the intermediate Grignard reagent), followed by a solution of benzyl N-(acetoxymethyl)carbamate (8.75 g., 0.0392 mole) in 20 ml. dry THF. After stirring at −78° C. for 30 minutes the reaction mixture was quenched with 8.5 ml. $CH_3CO_2H$, evaporated and the residue chromatographed on 600 g. silica gel, eluting with 1:19 ethyl acetate: $CHCl_3$, discarding the first 800 ml., then collecting 25 ml. fractions. Fractions 54–113 gave title product (9.9 g.). Center cuts 71–95 gave product of highest purity; 4.4 g.; pnmr/$CDCl_3$/TMS/delta (ppm): 1.30 (3H, t, J=7 Hz), 1.40 (3H, s), 1.52 (3H, s), 1.56 (3H, d, J=5.5), 3.71 (3H, br. m), 4.22 (2H, q, J=7 Hz), 4.32 (1H, s), 4.65 (1H, br. s), 5.10 (2H, s), 5.39 (1H, t, NH), 6.75 (1H, q, J=5.5), 7.33 (5H, s).

EXAMPLE 4

S-1-(Ethoxycarbonyloxy)ethyl 6-alpha-(Aminomethyl)penicillanate 1,1-Dioxide Hydrochloride Pd/C (10%, 3 g.) slurried in 30 ml. $H_2O$ was hydrogenated at 4 atmospheres for 15 minutes. The pH dropped from 9.2 to 4.5. Title product of the preceding Example (3.3 g.) in 50 ml. THF was added and hydrogenation at 4 atmospheres continued for 15 minutes. Pd/C (10%, 2 g.) was added and hydrogenation continued for an additional 15 minutes. The catalyst was recovered by filtration over diatomaceous earth with 30 ml. $H_2O$/70 ml. THF for wash. THF was evaporated from the combined filtrate and wash. The aqueous residue was combined with 75 ml. ethyl acetate, the pH adjusted from 6.2 to 8.0 with 0.5N NaOH, and the organic layer separated. The organic layer was combined with 50 ml. fresh $H_2O$, adjusted to pH 4.0 with 0.5N HCl and the aqueous layer separated and freeze dried to yield title product; 1.05 g.; pnmr/$D_2O$/DSS/delta (ppm): 1.28 (3H, t, J=7 Hz), 1.48 (3H, s), 1.58 (3H, d, J=5.5 Hz), 1.60 (3H, s), 3.65 (2H, m), 4.07 (1H, m), 4.26 (2H, q, J=7 Hz), 4.78 (1H, s), 5.13 (1H, d, J=2 Hz), 6.80 (1H, q, J=5.5).

EXAMPLE 5

R-1-(Ethoxycarbonyloxy)ethyl 6-alpha-(Benzyloxycarbonylaminomethyl)penicillanate 1,1-Dioxide R-1-(Ethoxycarbonyloxy)ethyl 6-alpha-bromopenicillanate 1,1-dioxide (10.2 g., 0.0238 mole) was reacted and isolated according to Example 3. The crude product was chromatographed on 700 g. silica gel, developed with 1000 ml. 1:19 ethyl acetate:$CHCl_3$ and then eluted with 1:9 ethyl acetate:$CHCl_3$, collecting 25 ml. fractions. Fractions 101–136 gave title product (6.8 g.). Center cuts 111–136 gave highest purity title product; 3.8 g.; pnmr/$CDCl_3$/TMS/delta (ppm): 1.30 (3H, t, J=7 Hz), 1.38 (3H, s), 1.54 (3H, d, J=5.5 Hz), 1.56 (3H, s), 3.71 (3H, br. m), 4.21 (2H, q, J=7 Hz), 4.37 (1H, s), 4.64 (1H, br. s), 5.09 (2H, s), 5.45 (1H, t, NH), 6.77 (1H, q, J=5.5 Hz), 7.30 (5H, s).

EXAMPLE 6

R-1-(Ethoxycarbonyloxy)ethyl 6-alpha-(Aminomethyl)penicillanate 1,1-Dioxide Hydrochloride By the procedure of Example 4, title product of the preceding Example (3.8 g.) was converted to present title product; 0.8 g.; pnmr/$D_2O$/DSS/delta (ppm): 1.27 (3H, t, J=7 Hz), 1.45 (3H, s), 1.58 (3H, d, J=5.5 Hz), 1.61 (3H, s), 3.64 (2H, m), 4.04 (1H, m), 4.13 (2H, q, J=7 Hz), 4.76 (1H, s), 5.12 (1H, d, J=2 Hz), 6.78 (1H, q, J=5.5).

EXAMPLE 7

Pivaloyloxymethyl 6-alpha-(Benzyloxycarbonylaminomethyl)penicillanate 1,1-Dioxide By the method of Examples 1, 3 and 5, pivaloyloxymethyl 6-alpha-bromopenicillanate 1,1-dioxide is converted to the corresponding Grignard reagent in situ and then reacted with an equivalent of benzyl N-acetoxymethylcarbamate, in the presence of a second equivalent of $CH_3MgBr$, to yield the present title product.

EXAMPLE 8 p-Toluenesulfonate Salt of Pivaloyloxymethyl 6-alpha-(Aminomethyl)penicillanate 1,1-Dioxide Method A Title product of the preceding Example (1.8 g., 3.53 mmoles) was hydrogenated in a mixture of THF (40 ml.) and $H_2O$ (20 ml.) over 1.8 g. of 10% Pd/C in the presence of pyridinium p-toluenesulfonate (1.77 g., 7.06 mmoles) at 50 psig for 1.5 hours. The catalyst was recovered by filtration over diatomaceous earth and the filtrate stripped of THF in vacuo, during which the title product crystallized, 1.2 g., m.p. 214°–215° C. (dec.); pnmr/DMSO-$d_6$/TMS 1.16 (9H, s), 1.32 (3H, s), 1.48 (3H, s), 2.28 (3H, s), 3.34 (2H, m), 3.82 (1H, m), 4.60 (1H, s), 5.14 (1H, d, J=2 Hz), 5.75 (2H, ABq), 7.23 (4H, ABq).

Anal. Calcd. for $C_{15}H_{24}O_7N_2S \cdot C_7H_7SO_3H$: C, 48.16; H, 5.88; N, 5.11. Found: C, 48.31; H, 6.11; N, 5.08.

Method B

Title product of the preceding Example (5.28 g., 10.35 mmoles) in 70 ml. THF was added to a slurry of 10% Pd/C (2.5 g.) which had been prehydrogenated in 70 ml. $H_2O$. The mixture was hydrogenated for 30 minutes at 50 psig. After recovery of the catalyst, p-toluenesulfonic acid (2.16 g.) in 5 ml. of $H_2O$ was added to the filtrate and the identical title product recovered by filtration, 4.08 g. (71.9%).

PREPARATION 1

6-alpha-Bromopenicillanic Acid 1,1-Dioxide

To 6,6-dibromopenicillanic acid 1,1-dioxide (117.3 g, 0.3 mole), stirring in a mixture of $H_2O$ (600 ml) and ethyl acetate (400 ml), was added in portions $NaHCO_3$ (75.6 g, 0.9 mole) and then $NaHSO_3$ (37.5 g, 0.36 mole). After stirring 1 hour, the pH was adjusted from 3.7 to 1.5 with concentrated HCl. The aqueous layer was separated and extracted 1×400 ml with fresh ethyl acetate. The combined organic layers were backwashed with brine, dried and evaporated to yield title product as a solid; 72 g (76.7%); m.p. 136°–137°, pnmr/$D_2O$-

NaHCO₃/delta: 1.48 (s, CH₃), 1.62 (s, CH₃), 4.28 (s, C.3-H), 5.12 (d, J=1.7, C.6-H), 5.37 (d, J=1.7, C.5-H).

PREPARATION 2

Benzyl 6-alpha-Bromopenicillanate 1,1-Dioxide

To title product of the preceding Example (24.3 g, 0.0779 mole) in 75 ml DMF was added TEA (7.87 g, 0.0779 mole) and benzyl bromide (13.32 g, 0.0779 mole). The mixture was stirred 16 hours, poured into 250 ml H₂O and extracted 2×200 ml ethyl acetate. The combined organic layers were washed with saturated NaHCO₃, H₂O and brine, dried, evaporated to dryness and the residue crystallized from ethyl acetate/hexane; 28.8 g (92%); m.p. 72°-74°; pnmr/CDCl₃/delta (ppm): 1.27 (s, CH₃), 1.53 (s, CH₃), 4.53 (s, C.3H), 4.8 (d, J=1.7, C.6-H), 5.27 (d, J=1.7, C.5-H), 5.3 (d, CH₂), 7.5 (s, C₆H₅).

PREPARATION 3

6-alpha-Bromopenicillanic Acid 6,6-Dibromopenicillanic acid (50 g., 0.1388 mole) was dissolved in a mixture of 400 ml. H₂O and 200 ml. ethyl acetate. NaHCO₃ (34.9 g., 0.4166 mole) was added portionwise, with gas evolution, followed by NaHSO₃ (17.3 g., 0.167 mole), also in portions. After stirring 15 minutes, the pH was adjusted from 6.6 to 1.8 with 6N HCl. The aqueous layer separated and extracted 2×200 ml. ethyl acetate. The organic layers were combined, backwashed 1×200 ml. H₂O, dried and evaporated to yield 6-alpha-bromopenicillanic acid as an oil, identical with the known product.

PREPARATION 4

R- and S-1-(Ethoxycarbonyloxy)ethyl 6-alpha-Bromopenicillanate 1,1-Dioxide 6-alpha-Bromopenicillanic acid (31 g.) was dissolved in 500 ml. CH₂Cl₂ and diluted with 200 ml. H₂O. NaHCO₃ (9.3 g.) was added, followed by the portionwise addition of tetrabutylammonium bisulfate (37.6 g.) while maintaining pH 7.5-8.0 with 2N NaOH. The organic layer was separated, washed with brine, dried and evaporated to yield tetrabutylammonium 6-alpha-bromopenicillanate as an oil (57.8 g.).

The oil and alpha-chlorodiethyl carbonate (25.3 ml.) were dissolved in 500 ml. acetone and stirred in the dark under N₂ for 36 hours. The reaction mixture was evaporated to a second oil and chromatographed on 1 Kg. silica gel, eluting with 1:4 hexane:CHCl₃ and collecting 20 ml. fractions. Fractions 33-100 were combined and evaporated to yield crude 1-(ethoxycarbonyloxy)ethyl 6-alpha-bromopenicillante as a third oil (41 g.).

The latter and m-chloroperbenzoic acid (30 g.) were taken into 500 ml. ethyl acetate, stirred under N₂ for 20 hours, washed in sequence with 3×50 ml., saturated NaHSO₃, 3×100 ml. saturated NaHCO₃ and 1×100 ml. brine, dried and evaporated. The resulting residue was chromatographed in 1 Kg. fresh silica gel, developed with 3 l. of 1:1 hexane:CHCl₃ and then eluted with CHCl₃ in 25 ml. fractions.

Less polar 81-160 were combined and evaporated to a white foam (15.8 g.) which crystallized on combining with 50 ml. ether and scratching to yield the title product of S-stereochemistry; 5.2 g.; m.p. 140°-143°; .tlc (1.9 ethyl acetate:CHCl₃) Rf 0.65; pnmr/CDCl₃/TMS/delta (ppm): 1.27 (3H, t, J=7 Hz), 1.46 (3H, s), 1.55 (3H, s), 1.58 (3H, d, J=5.5 Hz), 4.20 (2H, q, J=7 Hz), 4.35 (1H, s), 4.65 (1H, d, J=2 Hz), 5.09 (1H, d, J=2 Hz), 6.67 (1H, q, J=5.5).

Anal. Calcd. for C₁₃H₁₈O₈NSBr: C, 36.45; H, 4.23; N, 3.27. Found: C, 36.47; H, 4.30; N, 3.31.

More polar fractions 161-200 were combined and evaporated to a second while foam (4.1 g.) which also crystallized on combining with 50 ml. ether and scratching to yield the title product of R-stereo-chemistry; 2.8 g.; m.p. 114°-114.5°; tlc (1:9 ethyl acetate:CHCl₃) Rf 0.55; pnmr/CDCl₃/TMS/delta (ppm): 1.32 (3H, t, J=7 Hz), 1.45 (3H, s), 1.59 (3H, d, J=5.5), 1.62 (3H, s), 4.21 (2H, q, J=7 Hz), 4.41 (1H, s), 4.63 (1H, d, J=2 Hz), 5.11 (1H, d, J=2 Hz), 6.77 (1H, q, J=5.5).

Anal. Calcd. for C₁₃H₁₈O₈NSBr: C, 36.45; n, 4.23; N, 3.27. Found: C, 36.48; H, 4.26; N, 3.28.

PREPARATION 5

Pivaloyloxymethyl 6-alpha-Bromopenicillanate 6-alpha-Bromopenicillanic acid (10 g., 0.032 mole) was dissolved in 100 ml. CH₂Cl₂, combined with 30 ml. H₂O, and the pH adjusted to 8.3 with 2N NaOH. Tetrabutylammonium bisulfate (10.86 g., 0.032 mole) was added in portions, maintaining pH 8.0 with 2N NaOH. The organic layer was separated, dried and concentrated to yield intermediate tetrabutylammonium salt as an oil. The oil was dissolved in 100 ml. acetone, chloromethyl pivalate (5.11 ml., 0.035 mole) added and the mixture stirred 20 hours under N₂, then evaporated. The residue was chromatographed on 200 g. silica gel, eluting with CHCl₃ in 25 ml. fractions. Fractions 7-13 were combined and evaporated to yield title product as a crystalline residue; 3.5 g; pnmr/CDCl₃/TMS/delta (ppm): 1.23 (9H, s), 1.43 (3H, s), 1.57 (3H, s), 4.43 (1H, s), 4.68 (1H, d, J=2 Hz), 5.14 (1H, d, J=2 Hz), 5.83 (2H, q).

PREPARATION 6

Pivaloyloxymethyl 6-alpha-Bromopenicillanate 1,1-Dioxide

Method A

Title product of the preceding Example (4.1 g.) and m-chloroperbenzoic acid (3 g.) are combined in 50 ml. ethyl acetate and stirred under N₂ for 20 hours, washed in sequence with 3×5 ml. saturated NaHSO₃, 3×10 ml. saturated NaHCO₃ and 1×10 ml. brine, dried and evaporated to yield title product.

Method B 6-alpha-Bromopenicillanic acid 1,1-dioxide (30 g., 0.096 mole) was dissolved in DMF (100 ml.). Triethylamine (9.68 g., 0.096 mole) and chloromethyl pivalate (14.57 g., 0.096 mole) were added and the mixture stirred 1 day, then diluted with 400 ml. H₂O and 140 ml. ethyl acetate and the pH adjusted from 3.4 to 1.5 with dilute HCl. The aqueous layer was extracted 2×140 ml. fresh ethyl acetate. The organic layers were combined, washed 1×100 ml. saturated NaHCO₃, 1×100 ml. H₂O and 1×100 ml. brine and evaporated. The residual oil was triturated with hexane, taken up in CH₂Cl₂ and reevaporated to yield title product as a solid; 10.5 g; m.p. 94°-97°; pnmr/CDCl₃/TMS/delta (ppm): 1.25 (s, 9H), 1.45 (s, 3H), 1.62 (s, z3H), 4.57 (s, 1H), 4.85 (d, 1H, J=1.7 Hz), 5.3 (d, 1H, J=1.7 Hz), 6.0 (q, 2H).

I claim:

1. A process for the preparation of a compound of the formula

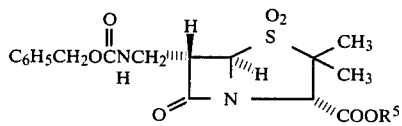
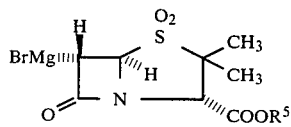

wherein $R^5$ is a conventional carboxy protecting group removable by hydrogenolysis, or a conventional ester forming radical which is hydrolyzable under physiological conditions, which comprises reacting a compound of the formula

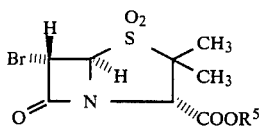

with substantially 2 molar equivalents of methylmagnesium bromide and then 1 molar equivalent of benzyl N-(acetoxymethyl)carbamate at −50° to −100° C. in an ethereal solvent.

2. A process of claim 1 wherein $R^5$ is:
benzyl
benzhydryl
gamma-butyrolacton-4-yl,
—$CHR^2OCOR^3$, or
—$CHR^2OCOOR^3$
wherein $R^2$ is hydrogen or methyl and $R^3$ is ($C_1$–$C_6$)alkyl.

3. The process of claim 2 wherein $R^5$ is benzyl.

4. The process of claim 2 wherein $R^5$ is pivaloyloxymethyl.

5. The process of claim 2 wherein $R^5$ is R- or S-1-(2-ethoxycarbonyloxy)ethyl.

6. The process of claim 5 wherein $R^5$ has R-stereochemistry.

7. The process of claim 5 wherein $R^5$ has S-stereochemistry.

8. A Grignard reagent of the formula wherein $R^5$ is a conventional carboxy protecting group removable by hydrogenolysis; or a conventional ester forming radical which is hydrolyzable under physiological conditions.

9. A compound of claim 8 wherein $R^5$ is:
benzyl;
benzhydryl;
gamma-butyrolacton-4-yl;
—$CHR^2OCOR^3$; or
—$CHR^2OCOOR^3$;
wherein $R^2$ is hydrogen or methyl and $R^3$ is ($C_1$–$C_6$)alkyl.

10. The compound of claim 9 wherein $R^5$ is benzyl.

11. The compound of claim 9 wherein $R^5$ is pivaloyloxymethyl.

12. The compound of claim 9 wherein $R^5$ is R- or S-1-(2-ethoxycarbonyloxy)ethyl.

13. The compound of claim 12 wherein $R^5$ has R-stereochemistry.

14. The compound of claim 12 wherein $R^5$ has S-stereochemistry.

15. R- or S-1-(Ethoxycarbonyloxy)ethyl 6-alpha-(benzyloxycarbonylaminomethyl)penicillanate 1,1-dioxide.

16. The compound of claim 15 having R-stereochemistry.

17. The compound of claim 15 having S-stereochemistry.

18. R- or S-1-(Ethoxycarbonyloxy)ethyl 6-alpha-(aminomethyl)penicillanate 1,1-dioxide, or a pharmaceutically acceptable acid addition salt thereof.

19. The compound of claim 18 having R-stereochemistry.

20. The compound of claim 18 having S-stereochemistry.

* * * * *